United States Patent
Bara et al.

(10) Patent No.: US 6,235,292 B1
(45) Date of Patent: *May 22, 2001

(54) TRANSFER-FREE MAKE-UP OR CARE COMPOSITION CONTAINING AN ORGANOPOLYSILOXANE AND A FATTY PHASE

(75) Inventors: Isabelle Bara, Paris; Frédéric Auguste, Chevilly-Larue, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/994,435

(22) Filed: Dec. 19, 1997

(30) Foreign Application Priority Data

Dec. 24, 1996 (FR) .................................................. 96 15984

(51) Int. Cl.⁷ ............................. A61K 7/04; A61K 7/021; A61K 7/025; A61K 31/74
(52) U.S. Cl. ............................. 424/401; 424/61; 424/63; 424/64; 424/78.02
(58) Field of Search .................................. 424/78.02, 61, 424/63, 401, 64; 514/844, 845

(56) References Cited

U.S. PATENT DOCUMENTS

| | | | |
|---|---|---|---|
| 4,980,167 | 12/1990 | Harashima et al. | 424/401 |
| 5,266,321 | * 11/1993 | Shukuzaki et al. | 424/401 |
| 5,919,468 | * 7/1999 | Bara | 424/401 |

FOREIGN PATENT DOCUMENTS

| | | |
|---|---|---|
| 1-250307 | 10/1989 | (JP) . |
| 2-243612 | 9/1990 | (JP) . |
| 39140 | 3/1992 | (JP) . |
| 7-258028 | 10/1995 | (JP) . |
| 7-267820 | 10/1995 | (JP) . |
| 61-194009 | 8/1996 | (JP) . |
| 9-801727 | 11/1996 | (JP) . |
| 8-319215 | 12/1996 | (JP) . |
| 9-143029 | 6/1997 | (JP) . |
| 9-175939 | 7/1997 | (JP) . |
| 9-175940 | 7/1997 | (JP) . |
| 9-227332 | 9/1997 | (JP) . |
| 9-315936 | 12/1997 | (JP) . |
| 9-328409 | 12/1997 | (JP) . |
| 10-194931 | 7/1998 | (JP) . |

OTHER PUBLICATIONS

Chemical Abstracts, vol. 126, No. 8, Abstract No. 108665 (1997).
Chemical Abstracts, vol. 126, No. 8, Abstract No. 108664 (1997).
Chemical Abstracts, vol. 126, No. 9, Abstract No. 122311 (1997).
Chemical Abstracts, vol. 110, No. 14, Abstract No. 121003 (1996).
Chemical Abstracts, vol. 124, No. 4, Abstract No. 37399 (1996).
English language Abstract of JP 61–194009.
English language Abstract of JP 1–250307.
English language Abstract of JP 7–258028.
English language Abstract of JP 7–267820.
English language Abstract of JP 8–301727.
English language Abstract of JP 8–319215.
English language Abstract of JP 9–143029.
English language Abstract of JP 9–175939.
English language Abstract of JP 9–175940.
English language Abstract of JP 9–315936.
English language Abstract of JP 9–328409.
English language Abstract of JP 10–194931 (Jul. 28, 1998).

* cited by examiner

Primary Examiner—Thurman K. Page
Assistant Examiner—S. Howard
(74) Attorney, Agent, or Firm—Finnegan, Henderson, Farabow, Garrett & Dunner, L.L.P.

(57) ABSTRACT

A transfer-free composition containing an organopolysiloxane and a fatty phase containing at least one oil which is volatile at room temperature, particularly a make-up or care composition for the lips or a make-up foundation composition both for the human face and the body. This composition is gentle to apply, spreads easily, is non-sticky and does not dry the skin or the lips.

26 Claims, No Drawings

TRANSFER-FREE MAKE-UP OR CARE COMPOSITION CONTAINING AN ORGANOPOLYSILOXANE AND A FATTY PHASE

The technology involved in this application is related to that disclosed in the following co-pending U.S. applications, filed on even date herewith:

(1) Title: Composition an Organopolysiloxane Gel Inventor: Isabelle Bara Ser. No.: 08/994,433
(2) Title: Non-migrating Make-up or Care Composition Containing an Organopolysiloxane and a Fatty Phase Inventors: Isabelle BARA and Frédéric AUGUSTE Ser. No.: 08/994,989

The specifications of these related applications are hereby specifically incorporated by reference.

The present invention relates to a care composition and/or make-up composition for human skin and/or lips, and in particular a lip coloring composition or foundation, in the form of a stick, a capel, or a cream.

The known lipstick and foundation compositions generally comprise fatty substances such as oils, pasty compounds and waxes, as well as a particulate phase generally composed of fillers and pigments.

When they are applied to the skin or the lips, these compositions have the drawback of transferring, i.e., of becoming at least partly deposited and leaving traces on certain supports with which they may be placed in contact, and in particular a glass, a cup, a cigarette, clothing or the skin. This results in mediocre persistence of the film applied to the skin or the lips, thus necessitating repeated application of the foundation or lipstick composition. Moreover, the appearance of these unacceptable traces, in particular on shirt and blouse collars, may put certain consumers off using this type of make-up.

Associated with this drawback of transfer of the lipstick compositions of the prior art, it should also be noted that films of these compositions have an annoying tendency to become dissolved in the plant oils generally used in certain cooked dishes such as salads with vinaigrette dressing, thus obliging consumers to reapply lipstick after the meal.

For several years, cosmeticians have been interested in lipstick compositions and, more recently, in foundation compositions which are "transfer-free". Thus, the company Shiseido envisaged, in its patent application JP-A-61-65809, transfer-free lipstick compositions containing from 1 to 70% by weight of a siloxysilicate resin (with a three-dimensional network) containing alkyl pendant chains of 1 to 6 carbon atoms or phenyl pendant chains, from 10 to 98% by weight of a volatile silicone oil containing a cyclic silicone chain and pulverulent fillers. Similarly, the company Noevier described, in document JP-A-62-61911, transfer-free lipstick, eye-liner and foundation compositions containing one or more volatile silicones combined with one or more hydrocarbon waxes.

Although entirely satisfactory as regards the transfer-free property, these compositions have the drawback of leaving on the lips, once the silicone oils have evaporated off, a film which becomes uncomfortable over time (sensation of drying and tautness), which puts a certain number of consumers off from using this type of lipstick. In order to improve the comfort of this type of composition, non-volatile silicone or non-silicone oils may be added, but, in this case, the transfer-free efficacy is lost.

More recently, the company Revlon envisaged, in its patent application EP-A-602,905, transfer-free lipsticks containing a cyclic or linear volatile silicone containing pendant methyl chains and a silicone resin containing a pendant esterified chain having from 12 to 18 carbon atoms. The film of lipstick which remains on the lips after the volatile silicone has evaporated off still has the drawback of being uncomfortable when applied, and especially of being too dry. Revlon has also envisaged, in its patent application EP-A-709,083, transfer-free foundations containing a volatile silicone combined with a siloxysilicate resin. These foundations also have the drawback of being relatively uncomfortable and dry over time.

One subject of the present invention is a care composition or make-up composition which makes it possible to overcome these drawbacks and makes it possible in particular to obtain a film which does not transfer and which has improved cosmetic properties when compared with those of the transfer-free products of the prior art, in particular slippery properties and properties of not causing tautness and of not drying the lips.

The invention applies not only to make-up products for the lips but also to care products and/or treatment products for the lips, as well as to make-up and care products for the skin.

Thus, a subject of the invention is a transfer-free make-up composition or care composition containing at least one solid, elastomeric, at least partially crosslinked organopolysiloxane combined with a fatty phase containing at least one oil which is volatile at room temperature.

The term "elastomeric" is understood to refer to a supple, deformable material having viscoelastic properties and in particular the consistency of a sponge or of a supple sphere.

The elastomeric organopolysiloxanes of the composition of the invention have noteworthy oil-gelling power. They do not dry the skin and afford good cosmetic properties. These novel elastomers lead to compositions which are comfortable when applied, soft and non-sticky to touch. This softness is due, on the one hand, to the texture of the organopolysiloxanes and, on the other hand, to their properties, which are comparable to those of microsponges trapping, in particular, non-volatile oils. These organopolysiloxanes further allow the non-transfer property by trapping the non-volatile oils.

After the volatile oil has evaporated off, these compositions lead to a homogeneous and uniform film having a light texture; it is comfortable, non-dry, is not taut and may be worn throughout the day.

The composition of the invention may be in the form of a paste, a solid or a cream. It may be an oil-in-water or water-in-oil emulsion, or a solid or supple anhydrous gel.

The elastomeric organopolysiloxanes in accordance with the invention are partially or totally crosslinked and of three-dimensional structure. When included in a fatty phase, they become converted, depending on the fatty phase content used, from a product of spongy appearance when they are used in the presence of low fatty phase contents, into a homogeneous gel in the presence of larger amounts of fatty phase. Gelling of the fatty phase by these elastomers may be total or partial.

The elastomers of the invention are generally in the form of a gel comprising an elastomeric organopolysiloxane of three-dimensional structure, included in at least one hydrocarbon oil and/or a silicone oil.

The elastomeric organopolysiloxanes according to the invention may be selected from the crosslinked polymers described in European application EP-A-0,295,886, the disclosure of which is specifically incorporated by reference herein. According to that application, they are obtained by addition reaction and crosslinking, in the presence of a platinum-type catalyst, of at least (a) an organopolysiloxane having at least two $C_2$–$C_6$ lower alkenyl groups per molecule; and (b) an organopolysiloxane having at least two hydrogen atoms linked to a silicon atom per molecule.

The elastomeric organopolysiloxanes according to the invention may also be selected from those described in U.S. Pat. No. 5,266,321, the disclosure of which is specifically incorporated by reference herein. According to that patent, they are selected in particular from:

i) organopolysiloxanes comprising $R_2SiO$ and $RSiO_{1.5}$ units and optionally $R_3SiO_{0.5}$ and/or $SiO_2$ units in which the radicals R, independently of each other, represent a hydrogen, an alkyl such as methyl, ethyl or propyl, an aryl such as phenyl or tolyl, an unsaturated aliphatic group such as vinyl, the weight ratio of the units $R_2SiO$ to the units $RSiO_{1.5}$ ranging from 1:1 to 30:1;

ii) organopolysiloxanes which are insoluble and swellable in silicone oil, obtained by addition of an organohydrogenopolysiloxane (1) and of an organopolysiloxane (2) having unsaturated aliphatic groups such that the amount of hydrogen or of unsaturated aliphatic groups in (1) and (2) respectively ranges from 1 to 20 mol % when the organopolysiloxane is non-cyclic and from 1 to 50 mol % when the organopolysiloxane is cyclic.

The organopolysiloxanes of the composition of the invention are, for example, those marketed under the names KSG6 from Shin-Etsu, TREFIL E-505C or TREFIL E-506C from Dow-Corning, GRANSIL from Grant Industries (SR-CYC, SR DMF 10, SR-DC556) or those marketed in the form of preconstituted gels (KSG15, KSG17, KSG16, KSG18 from Shin-Etsu, GRANSIL SR 5CYC gel, GRANSIL SR DMF 10 gel, GRANSIL SR DC556 gel, SF 1204 and JK 113 from General Electric). The mixture of these commercial products may also be used.

The organopolysiloxane is preferably present in the organopolysiloxane/fatty phase mixture in the form of a homogeneous gel at a concentration ranging from 0.3 to 40% of the total weight of the composition. Preferably, the elastomer represents, as active material, from 0.1 to 20% in the composition and more preferably from 0.3 to 15%.

The fatty phase may be of any nature; it generally contains oils (products which are fluid at room temperature) which may be silicone, fluoro, fluorosilicone or hydrocarbon oils which are optionally partially siliconated.

The best gelling is achieved with silicone oils or partially siliconated oils, apolar oils and sparingly polar oils and a few polar oils which do not harm the stability of the system.

According to the invention, the fatty phase contains one or more oils which are volatile at room temperature. The term volatile oil is understood to refer to an oil which can evaporate on contact with the skin or the lips.

These volatile oils may be hydrocarbon oils, silicone oils or mixtures thereof. The volatile silicones are, for example, silicones containing a linear silicone structure and units with a pendant alkyl chain and/or an alkyl chain at the end of the silicone structure, these alkyl chains being linear or branched and containing from 3 to 10 carbon atoms. The volatile silicones with an alkyl chain especially have the formula (I) below:

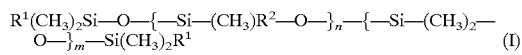

in which:

$R^1$ and $R^2$ are, independently, hydrogen, methyl or a chain having from 3 to 10 carbon atoms, n and m being integers ranging from 0 to 10, on condition that if $R^1$ is hydrogen or methyl, n is other than 0 and $R^2$ represents an alkyl chain of 3 to 10 carbon atoms.

As alkylated volatile silicones which may be used in the invention, mention may be made of alkyl heptamethyltrisiloxanes with a $C_4$, $C_5$, $C_6$, $C_7$ or $C_8$ alkyl group, such as, for example, hexylheptamethyltrisiloxane of formula: $(CH_3)_3$—Si—O—Si$(CH_3)(C_6H_{13})$—O—Si—$(CH_3)_3$; octyl heptamethyltrisiloxane of formula: $(CH_3)_3$—Si—O—Si$(CH_3)$$(C_8H_{15})$—O—Si$(CH_3)_3$; and mixtures thereof.

As volatile silicones which may be used in the invention, mention may also be made of polydimethylsiloxanes with a linear chain having from 2 to 6 silicon atoms. These silicones satisfy formula (I) with m having a value of 0, n having a value from 0 to 6 and $R^1$ and $R^2$ simultaneously representing $CH_3$ or phenyl. Mention may be made, for example, of methylpolysiloxanes such as hexamethyidisiloxane, methylphenylpolysiloxanes, ethylpolysiloxanes, ethylmethylpolysiloxanes, ethylphenylpolysiloxanes, hydroxymethylpolysiloxanes and mixtures thereof.

Cyclic silicones having from 3 to 7 units —$R_{1'}R_{2'}SiO$—, with $R_{1'}$ and $R_{2'}$ independently representing hydrogen, methyl, ethyl or phenyl, may also be used as volatile silicones. Mention may be made, for example, of octamethylcyclopentasiloxane, decamethylcyclopentasiloxane or mixtures thereof.

As volatile hydrocarbon oils which may be used in the invention, mention may be made of $C_3$ to $C_{20}$ isoparaffins, for instance the $C_{12}$ isoparaffin known as isododecane and $C_{16}$ isoparaffin, for instance isohexadecane.

The volatile oils preferably represent from 1 to 50% of the total weight of the composition, and more preferably from 30 to 50%.

In addition to the volatile oils mentioned above, the composition of the invention may preferably comprise non-volatile fatty substances usually used in the field of application envisaged and, in particular, non-volatile oils and waxes. These non-volatile oils improve the comfort of the composition.

As non-volatile oils which may be used in the invention, mention may be made, in particular, of:

hydrocarbon oils of animal origin such as perhydrosqualene;

plant hydrocarbon oils such as liquid triglycerides of fatty acids, for example sunflower oil, corn oil, soybean oil, marrow oil, grapeseed oil, sesame oil, hazelnut oil, apricot oil, macadamia oil, castor oil, avocado oil, caprylic/capric acid triglycerides such as those sold by the company Stearineries Dubois or those sold under the names MIGLYOL 810, 812 and 818 by the company Dynamit Nobel;

oils of formula $R_9COOR_{10}$ in which $R_9$ represents a higher fatty acid residue containing from 7 to 19 carbon atoms and $R_{10}$ represents a branched hydrocarbon chain containing from 3 to 20 carbon atoms, such as, for example, Purcellin oil;

linear or branched hydrocarbons of mineral or synthetic origin, such as non-volatile liquid paraffins and derivatives thereof, petroleum jelly, polydecenes, and hydrogenated polyisobutene such as parleam;

synthetic esters and ethers such as isopropyl myristate, octanoates, decanoates or ricinoleates of alcohols or of polyalcohols;

fatty alcohols such as octyidodecanol or oleyl alcohol;

partially hydrocarbonated and/or siliconated fluoro oils such as those described in Japanese patent document JP-A-2-295912, the disclosure of which is specifically incorporated by reference herein;

silicone oils such as linear, non-volatile polymethylsiloxanes which are liquid or pasty at room temperature, phenyldimethicones, phenyltrimethicones and polymethylphenylsiloxanes;

mixtures thereof.

The non-volatile oils preferably represent from 0 to 50% of the total weight of the composition, more preferably from 0 to 35%, and are selected as a function of their compatibility with the elastomeric organopolysiloxanes.

Advantageously, the composition according to the invention may contain hydrocarbon, fluoro or silicone waxes or mixtures thereof, which may be solid or semi-solid (in the form of a paste) at room temperature. These waxes may be of plant, mineral, animal and/or synthetic origin. In particular, these waxes preferably have a melting point of greater than 25° C. and, more preferably, greater than 45° C.

The silicone waxes may be waxes having a silicone structure and units containing one or more pendant alkyl or alkoxy chains and/or alkyl or alkoxy chains at the end of the silicone structure, these chains being linear or branched and containing from 10 to 45 carbon atoms. These waxes are respectively known as aklyldimethicones and alkoxydimethicones. Moreover, these alkyl chains may contain one or more ester functions.

Among the silicone waxes which may be used in the invention, mention may be made of the behenoxydimethicone, such as that sold by Goldschmidt under the name ABIL WAX 2440; stearyldimethicone, such as that sold by Dow Corning under the name DC 2503; cetyidimethicone, such as that sold by Goldschmidt under the name ABIL WAX 9814; stearylmethicone, such as that sold by Goldschmidt under the name ABIL WAX 9809; $C_{24}$–$C_{28}$ alkyldimethicone, such as that sold by Goldschmidt under the name ABIL WAX 9810; $C_{30}$–$C_{45}$ alkylmethicone, such as that sold by Goldschmidt under the name ABIL WAX 9811; stearoxydimethicone, such as that sold by Goldschmidt under the name ABIL WAX 2434; dimethicone behenate, such as that sold by Rhône Poulenc under the name MYRASIL WAX B.

As other silicone waxes which may be used in the invention, mention may be made of alkyldimethicone copolymers. These compolymers are especially those described in European Patent Application EP-A-527,594, U.S. Pat. No. 5,061,481 and U.S. Pat. No. 5,397,566, the disclosures of which are specifically incorporated by reference herein. Mention may also be made of silicone waxes modified with fluoro chains, such as those described in European Patent Application EP-A-661,042, the disclosure of which is specifically incorporated by reference herein.

As other waxes which may be used in the invention, mention may be made of waxes of animal origin such as lanolin, beeswax; plant waxes, such as carnauba wax or candelilla wax; mineral waxes, for example paraffin wax, lignite wax or microcrystalline waxes, ceresine or ozokerite; synthetic waxes such as polyethylene waxes.

These fatty substances may be selected in a variety of ways by those skilled in the art in order to prepare a composition having the desired properties, for example of consistency or of texture.

In particular, the presence of waxes makes it possible to ensure good mechanical strength, in particular when the composition is in the form of a stick.

In general, the composition may comprise wax in a proportion preferably of from 0 to 50% of the total weight of the composition, and more preferably of 10 to 30%.

The composition of the invention may also comprise any additive commonly used in the field concerned, such as water-soluble or liposoluble dyes, antioxidants, essential oils, preserving agents, cosmetic or dermatological active agents, moisturizers, vitamins, essential fatty acids, lipophilic sunscreens, and liposoluble polymers, in particular hydrocarbons such as polyalkylenes. These additives may be present in the composition preferably in a proportion of from 0 to 20% of the total weight of the composition, and more preferably from 0 to 10%.

Obviously, a person skilled in the art will take care to select the optional complementary additives and/or the amount thereof such that the advantageous properties of the composition according to the invention are not, or are not substantially, adversely affected by the addition envisaged. In particular, these additives must not harm the homogeneity, the stability, the comfort or the "transfer-free" nature of the composition.

The compositions according to the invention may especially be in the form of a stick or a tube or in the form of a supple or cast paste, or alternatively in the form of a gelled oily liquid or a cream.

The composition according to the invention may be in the form of a colored make-up product for the skin, in particular a foundation, a blusher, an eyeshadow, a concealer stick or make-up for the lips such as a lipstick. They may also be in non-colored form, optionally containing cosmetic or dermatological active agents. In this case, they may be used as a care base for the lips (lip balms for protecting the lips against the cold and/or the sun and/or the wind) or a fixing base to be applied over a standard lipstick. The fixing base thus forms a protective film over the film of lipstick, which limits its transfer.

The composition of the invention may also be in the form of a dermatological or skincare composition, or in the form of an antisun composition.

Obviously, the composition of the invention must be cosmetically or dermatologically acceptable, that is to say non-toxic and capable of being applied to human skin or mucous membranes (lips, inner edge of the eyelids).

Preferably, the composition of the invention may comprise a particulate phase which is preferably present in a proportion of from 0 to 35% of the total weight of the composition, more preferably from 5 to 25%, and which may comprise pigments and/or pearlescent agents and/or fillers usually used in cosmetic compositions.

The term pigments should be understood to mean white or colored, inorganic or organic particles which are insoluble in wax and the volatile silicone, intended to color and/or opacify the composition. The term charges should be understood to mean colorless or white, inorganic or synthetic, lamellar or non-lamellar particles. The term pearlescent agents should be understood to mean iridescent particles, in particular those produced by certain molluscs in their shell or synthesized. These fillers and pearlescent agents serve to modify the texture of the composition as well as the matte effect/sheen.

The pigments may preferably be in the composition in a proportion of from 0 to 25% of the weight of the final composition, and more preferably in a proportion of 5 to 15%. As inorganic pigments which may be used in the invention, mention may be made of titanium oxide, zirconium oxide or cerium oxide, as well as zinc oxide, iron oxide or chromium oxide and ferric blue. Among the organic pigments which may be used in the invention, mention may be made of carbon black and barium, strontium, calcium and aluminum lakes.

The pearlescent agents may preferably be present in the composition in a proportion of from 0 to 20% of the total weight of the composition, more preferably in a high content of from about 8 to 15%. Among the pearlescent agents which may be used in the invention, mention may be made of mica coated with titanium oxide, with iron oxide, with natural pigment or with bismuth oxychloride such as colored titanium mica.

The fillers may preferably be present in a proportion of from 0 to 35% of the total weight of the composition, more preferably 5 to 15%. Mention may be made in particular of talc, mica, silica, kaolin, nylon powders (in particular ORGASOL), polyethylene powders, Teflon, starch, boron nitride, copolymer microspheres such as EXPANCEL (Nobel Industrie), polytrap (Dow Corning) and silicone resin microbeads (TOSPEARL from Toshiba, for example).

More specifically, the subject of the invention is an anhydrous, transfer-free lipstick or foundation characterized in that it contains at least one solid, elastomeric, at least partially crosslinked organopolysiloxane combined with a fatty phase containing at least one oil which is volatile at room temperature, and pigments and/or fillers.

The composition according to the invention may be manufactured by heating one or more elastomeric organopolysiloxanes combined with one or more oils, one or more waxes, one or more pigments, one or more fillers and/or one or more other additives at a temperature above the highest melting point of the waxes, after which the molten mixture is cast in a mold. This process makes it possible to obtain a composition in the form of a solid stick or capel.

The composition may also be obtained by extrusion as described in European Patent Application EP-A-667,146, the disclosure of which is specifically incorporated by reference herein. This process involves blending the paste (waxes+oils+additives+pigments) during the cooling phase in order to create in the bulk zones for crushing the paste using a cylinder mill or a screw extruder-mixer. This process makes it possible to obtain a composition in the form of a soft paste.

The subject of the invention is also the use of the combination of a silicone which is volatile at room temperature and a solid, at least partially crosslinked, elastomeric organopolysiloxane in a composition in order to reduce the transfer of the said composition.

The subject of the invention is also a process for limiting and/or preventing the transfer of a make-up or care composition for the skin or the lips onto a substrate other than the said skin and the said lips, this process involving introducing at least one solid, at least partially crosslinked, elastomeric organopolysiloxane and an oil which is volatile at room temperature into the composition.

The invention is illustrated in greater detail in the examples which follow and which are in no way limiting. The percentages are given on a weight basis.

EXAMPLE 1

| Phenyltrimethicone | 22% |
|---|---|
| Stearyldimethicone | 4% |
| Jojoba oil | 1% |
| Elastomeric organopolysiloxane (KSG6) | 5% |
| Pigments | 8% |
| Pplyethylene wax | 20% |
| Volatile cyclomethicone | 40% |

Preparation:

The organopolysiloxane was swollen in the oils which are non-volatile at room temperature. The pigments were then impasted into the gel obtained at 60° C. and the mixture was then ground in a three-cylinder mill at room temperature. The ground product was mixed with the waxes at 95° C., after which the volatile oil was added and the mixture was cast in a mould.

A cast lipstick of pleasant texture, which spread well and uniformly was obtained.

Test:

This composition was applied to the left side of the lips of several individuals. For comparison, a transfer-free lipstick of the prior art, not containing any elastomeric organopolysiloxane or a fatty phase, was applied to the right side of said lips.

The lipsticks were left to dry at room temperature for 30 minutes, after which the lips were pressed fully against a sheet of paper.

A very faint, barely perceptible trace of lipstick was observed on all of the sheets of paper, both for the composition of the invention and for the composition of the prior art. In addition, the film obtained on the lips with the composition of the invention was accepted as being more comfortable and less dry than that obtained with the composition of the prior art.

EXAMPLE 2

| | |
|---|---|
| Elastomeric organopolysiloxane (KSG 6) | 10% |
| Behenoxydimethicone (ABIL WAX 2440) | 5% |
| Polyethylene wax | 20% |
| Alkyldimethicone (X2 5514 from Dow Corning) | 20% |
| Alkyldimethicone (X2 1731 from Dow Corning) | 55% |

This composition was prepared as in Example 1.

This composition was in a form of pleasant texture, which spread well and applied uniformly. The film obtained on the lips was comfortable to wear over time.

What is claimed is:

1. A process for limiting and/or preventing the transfer of a colored make-up composition for the skin or the lips comprising, introducing into said colored make-up composition at least one solid, at least partially crosslinked, elastomeric organopolysiloxane combined with a fatty phase containing at least one oil, wherein said at least one oil is volatile at room temperature, wherein said colored make-up composition comprises at least one coloring agent.

2. A process according to claim 1, wherein said at least one volatile oil is present in a concentration ranging from 1 to 50% by weight relative to the total weight of said colored make-up composition.

3. A process according to claim 2, wherein said at least one volatile oil is present in a concentration ranging from 30 to 50% by weight relative to the total weight of said colored make-up composition.

4. A process according to claim 1, wherein said at least one oil is selected from volatile silicone oils containing a linear silicone structure and units with a pendant alkyl chain and/or an alkyl chain at the end of the silicone structure, wherein said alkyl chains are linear or branched and contain from 3 to 10 carbon atoms; polydimethylsiloxanes with a linear chain having from 2 to 6 silicon atoms; cyclic silicones having from 3 to 7 units —$R_1R_2SiO$—, wherein $R_1$. and $R_2$. independently represent hydrogen, methyl, ethyl or phenyl; and $C_3$–$C_{20}$ isoparaffins.

5. A process according to claim 1, wherein said elastomeric organopolysiloxane is obtained by addition reaction and crosslinking, in the presence of a catalyst, of at least:

(a) an organopolysiloxane having at least two $C_2$–$C_6$ lower alkenyl groups per molecule; and (b) an organopolysiloxane having at least two hydrogen atoms linked to a silicon atom per molecule.

6. A process according to claim 1, wherein said elastomeric organopolysiloxane is selected from:

(i) organopolysiloxanes comprising $R_2SiO$ and $RSiO_{1.5}$ units and optionally $R_3SiO_{0.5}$ and/or $SiO_2$ units wherein the radicals R, independently of each other, represent a hydrogen, an alkyl, an aryl, an unsaturated aliphatic group, wherein the weight ratio of said $R_2SiO$ units to said $RSiO_{1.5}$ units ranges from 1:1 to 30:1; and (ii) organopolysiloxanes which are insoluble in silicone oil, obtained by addition of an organohydrogenopolysiloxane and of an organopolysiloxane having unsaturated aliphatic groups, wherein the amount of hydrogen or of unsaturated aliphatic groups in said organohydrogenopolysiloxane and said organopolysiloxane respectively ranges from 1 to 20 mol % when the organopolysiloxane is non-cyclic and from 1 to 50 mol % when the organopolysiloxane is cyclic.

7. A process according to claim 1, wherein said elastomeric organopolysiloxane is present in the form of a homogeneous gel at a concentration ranging from 0.3 to 40% by weight relative to the total weight of said colored make-up composition.

8. A process according to claim 1, wherein said elastomeric organopolysiloxane is present in the form of a homogeneous gel at a concentration ranging from 0.1 to 20% by weight relative to the total weight of said colored make-up composition.

9. A process according to claim 8, wherein said elastomeric organopolysiloxane is present in the form of a homogeneous gel at a concentration ranging from 0.3 to 15% by weight relative to the total weight of said colored make-up composition.

10. A process according to claim 1, wherein said at least one oil is selected from silicone oils and hydrocarbon oils.

11. A process according to claim 1, wherein said colored make-up composition further comprises at least one non-volatile fatty substance.

12. A process according to claim 11, wherein said at least one non-volatile fatty substance is selected from non-volatile oils and waxes.

13. A process according to claim 12, wherein said at least one non-volatile fatty substance is selected from non-volatile oils and is present in a concentration ranging up to 50% by weight relative to the total weight of said colored make-up composition.

14. A process according to claim 12, wherein said non-volatile oils are selected from hydrocarbon oils of animal or plant origin; oils of formula $R_9COOR_{10}$ wherein $R_9$ represents a higher fatty acid residue containing from 7 to 19 carbon atoms and $R_{10}$ represents a branched hydrocarbon chain containing from 3 to 20 carbon atoms; linear or branched hydrocarbons of mineral or synthetic origin; fatty alcohols; synthetic esters and ethers; silicone oils; and fluoro oils which are optionally partially hydrocarbonated and/or siliconated.

15. A process according to claim 14, wherein said silicone oils are selected from linear polymethylsiloxanes which are liquid or pasty at room temperature; phenyldimethicones; phenyltrimethicones; and polymethylphenylsiloxanes.

16. A process according to claim 12, wherein said at least one non-volatile fatty substance is a non-volatile wax selected from hydrocarbon waxes, fluoro waxes and silicone waxes.

17. A process according to claim 16, wherein said at least one non-volatile fatty substance is a non-volatile wax present in a concentration ranging up to 50% by weight relative to the total weight of said colored make-up composition.

18. A process according to claim 17, wherein the concentration of said non-volatile wax ranges from 10 to 30% by weight relative to the total weight of said colored make-up composition.

19. A process according to claim 1, wherein said colored make-up composition further comprises a particulate phase.

20. A process according to claim 19, wherein said particulate phase is present in a concentration ranging up to 35% by weight relative to the total weight of the colored make-up composition.

21. A process according to claim 20, wherein said particulate phase is present in a concentration ranging from 5 to 25% by weight relative to the total weight of the colored make-up composition.

22. A process according to claim 1, wherein said colored make-up composition is in the form of a paste, a solid, a cream, an oil-in-water emulsion, a water-in-oil emulsion or an anhydrous gel.

23. A process according to claim 1, wherein said colored make-up composition is in the form of a stick, a tube, a supple or cast paste, a cream or a gelled oily liquid.

24. A process according to claim 1, wherein said colored make-up composition further comprises at least one cosmetic or dermatological active agent.

25. A process according to claim 1, wherein said colored make-up composition is in the form of a foundation, a blusher, an eyeshadow, a concealer product, a lipstick, a care base, a fixing base for the lips, a dermatological products a skincare product, or an antisun composition.

26. A process for treating human skin or lips comprising applying a colored make-up composition made according to claim 1 to the skin or the lips.

* * * * *

UNITED STATES PATENT AND TRADEMARK OFFICE
CERTIFICATE OF CORRECTION

PATENT NO. : 6,235,292 B1
DATED : May 22, 2001
INVENTOR(S) : Isabelle Bara et al.

Page 1 of 1

It is certified that error appears in the above-identified patent and that said Letters Patent is hereby corrected as shown below:

<u>Column 9, claim 4,</u>
Line 44-45, "R., and $R_2$." should read -- $R_1$· and $R_2$· --

<u>Column 9, claim 6,</u>
Line 67, after "unsat", insert a hyphen.

<u>Columns 11 and 12, claim 25,</u>
Line 11, "dermatological products" should read -- dermatological product, --.

Signed and Sealed this

Fifth Day of March, 2002

Attest:

Attesting Officer

JAMES E. ROGAN
Director of the United States Patent and Trademark Office